(12) United States Patent
Mueller

(10) Patent No.: US 10,045,813 B2
(45) Date of Patent: *Aug. 14, 2018

(54) JAW ROLL JOINT

(71) Applicant: COVIDIEN LP, Mansfield, MA (US)

(72) Inventor: Peter M. Mueller, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 438 days.

This patent is subject to a terminal disclaimer.

(21) Appl. No.: 14/747,277

(22) Filed: Jun. 23, 2015

(65) Prior Publication Data

US 2015/0282876 A1 Oct. 8, 2015

Related U.S. Application Data

(63) Continuation of application No. 13/847,350, filed on Mar. 19, 2013, now Pat. No. 9,084,607, which is a
(Continued)

(51) Int. Cl.
*A61B 18/12* (2006.01)
*A61B 18/14* (2006.01)
(Continued)

(52) U.S. Cl.
CPC .......... *A61B 18/1445* (2013.01); *A61B 17/29* (2013.01); *A61B 18/1492* (2013.01);
(Continued)

(58) Field of Classification Search
CPC . A61B 17/29; A61B 17/320016; A61B 18/14; A61B 18/1442; A61B 18/1445; A61B 2017/00477; A61B 2017/2905; A61B 2017/2927; A61B 2017/2929; A61B 2017/293; A61B 2017/003;
(Continued)

(56) References Cited

U.S. PATENT DOCUMENTS

| 5,174,300 A | 12/1992 | Bales et al. |
| 5,176,142 A | 1/1993 | Mason |

(Continued)

FOREIGN PATENT DOCUMENTS

| JP | 6114075 | 4/1994 |
| JP | 2007215896 A | 8/2007 |

(Continued)

OTHER PUBLICATIONS

European Office Action dated Dec. 23, 2016, issued in EP Application No. 10 189 416.
(Continued)

*Primary Examiner* — Daniel Fowler

(57) ABSTRACT

A surgical instrument includes a handle, and an elongated shaft extending from the handle. An end effector extending from the elongated shaft is in communication with a source of electrosurgical energy and defines an end effector axis. A roll joint couples the end effector to the elongated shaft and includes a first tubular structure extending distally from the elongated shaft and a second tubular structure rotatably coupled to the first tubular structure. The second tubular structure supports the end effector such that the end effector is rotatable about the end effector axis.

16 Claims, 16 Drawing Sheets

Related U.S. Application Data continuation of application No. 12/609,284, filed on Oct. 30, 2009, now Pat. No. 8,398,633.

(51) Int. Cl.
*A61B 17/29* (2006.01)
*A61B 34/00* (2016.01)
*A61B 17/32* (2006.01)
*A61B 17/00* (2006.01)
*A61B 18/00* (2006.01)
*A61B 18/18* (2006.01)

(52) U.S. Cl.
CPC ...... *A61B 34/71* (2016.02); *A61B 17/320016* (2013.01); *A61B 18/14* (2013.01); *A61B 2017/003* (2013.01); *A61B 2017/00323* (2013.01); *A61B 2017/00477* (2013.01); *A61B 2017/293* (2013.01); *A61B 2017/2905* (2013.01); *A61B 2017/2927* (2013.01); *A61B 2018/0063* (2013.01); *A61B 2018/00178* (2013.01); *A61B 2018/00601* (2013.01); *A61B 2018/1412* (2013.01); *A61B 2018/1455* (2013.01); *A61B 2018/1861* (2013.01)

(58) Field of Classification Search
CPC A61B 2017/00323; A61B 2018/00178; A61B 2018/0063; A61B 2018/00601; A61B 2018/1412; A61B 2018/1455; A61B 2018/1861; A61B 2019/2242; A61B 2018/006
See application file for complete search history.

(56) References Cited

U.S. PATENT DOCUMENTS

| | | |
|---|---|---|
| 5,209,747 A | 5/1993 | Knoepfler |
| 5,330,502 A | 7/1994 | Hassler et al. |
| 5,374,277 A | 12/1994 | Hassler |
| 5,431,323 A | 7/1995 | Smith et al. |
| 5,439,478 A | 8/1995 | Palmer |
| 5,478,003 A * | 12/1995 | Green ............. A61B 17/07207 227/176.1 |
| 5,704,534 A | 1/1998 | Huitema et al. |
| 5,766,169 A | 6/1998 | Fritzsch et al. |
| 6,558,385 B1 | 5/2003 | McClurken et al. |
| 7,083,615 B2 | 8/2006 | Peterson et al. |
| 7,083,618 B2 | 8/2006 | Couture et al. |
| 7,101,372 B2 | 9/2006 | Dycus et al. |
| 7,101,373 B2 | 9/2006 | Dycus et al. |
| 7,147,650 B2 | 12/2006 | Lee |
| 8,064,978 B2 | 11/2011 | Anderson et al. |
| 9,084,607 B2 | 7/2015 | Mueller |
| 2002/0188294 A1 | 12/2002 | Couture et al. |
| 2003/0060927 A1* | 3/2003 | Gerbi .................. G06F 19/3406 700/245 |
| 2004/0087940 A1 | 5/2004 | Jahns et al. |
| 2006/0279534 A1 | 12/2006 | Powers et al. |
| 2007/0049966 A1* | 3/2007 | Bonadio .......... A61B 17/00234 606/206 |
| 2009/0312773 A1 | 12/2009 | Cabrera et al. |
| 2010/0160929 A1 | 6/2010 | Rogers et al. |

FOREIGN PATENT DOCUMENTS

| | | |
|---|---|---|
| JP | 2008253351 A | 10/2008 |
| WO | 2008/045348 A2 | 4/2008 |

OTHER PUBLICATIONS

European Office Action dated Mar. 21, 2016, issued in European Application No. 10 189 416.
Japanese Preliminary Report dated Apr. 18, 2014 issued in Japanese Appln. No. 2010-245691.
European Search Report dated Mar. 13, 2015 issued in EP Appin. No. 10189416.

* cited by examiner

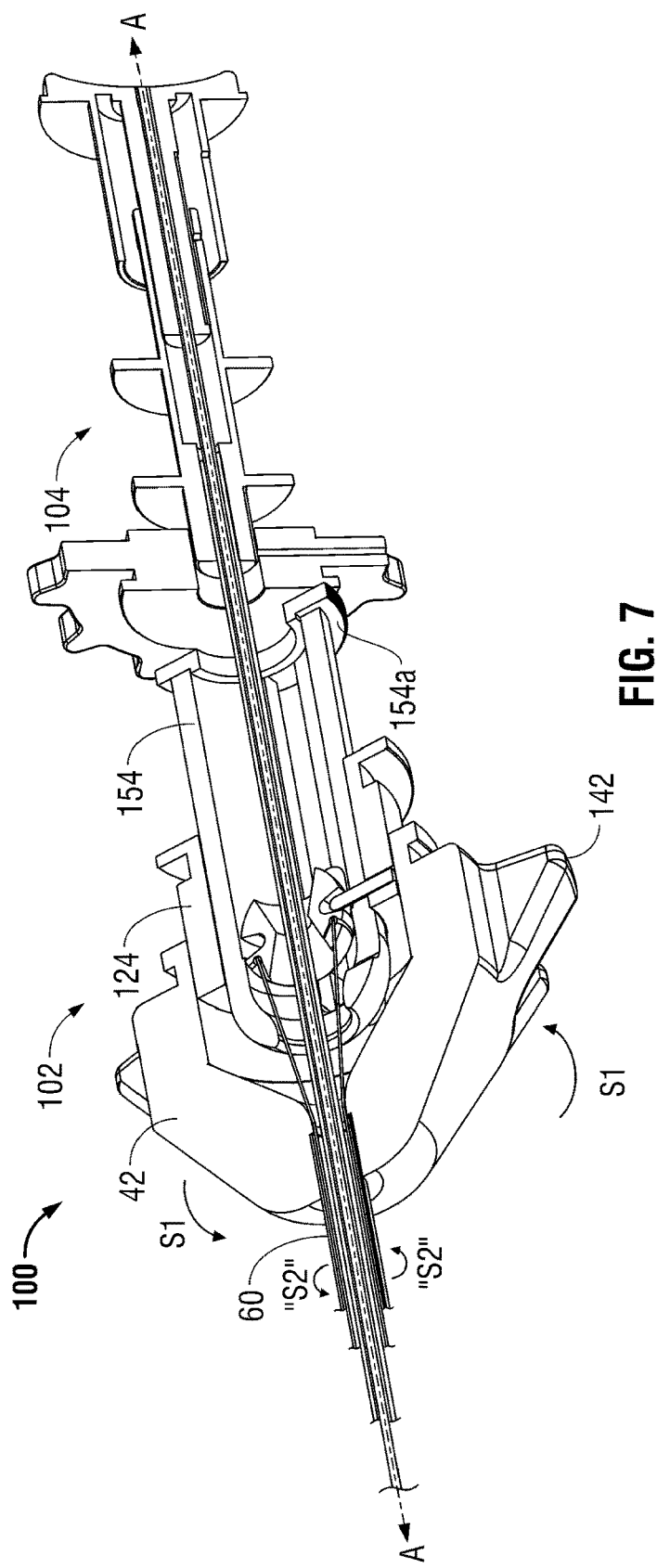

JAW ROLL JOINT

CROSS-REFERENCE TO RELATED APPLICATIONS

This application claims the benefit as a continuation application of U.S. patent application Ser. No. 13/847,350, filed Mar. 19, 2013, which is a continuation of U.S. patent application Ser. No. 12/609,284, filed Oct. 30, 2009, now U.S. Pat. No. 8,398,633. The entire contents of each of the above applications is hereby incorporated by reference.

BACKGROUND

1. Technical Field

The present disclosure relates to a surgical apparatus having an elongated shaft for laparoscopic and endoscopic procedures. In particular, the disclosure relates to a surgical apparatus having a roll joint permitting an end effector to rotate relative to a distal portion of the elongated shaft.

2. Background of Related Art

Typically in a laparoscopic, an endoscopic, or other minimally invasive surgical procedure, a small incision or puncture is made in a patient's body. A cannula is then inserted into a body cavity through the incision, which provides a passageway for inserting various surgical devices such as scissors, dissectors, retractors, or similar instruments. To facilitate operability through the cannula, instruments adapted for laparoscopic surgery typically include a relatively narrow shaft supporting an end effector at its distal end and a handle at its proximal end. Arranging the shaft of such an instrument through the cannula allows a surgeon to manipulate the handle from outside the body to cause the end effector to carry out a surgical procedure at a remote internal surgical site. This type of laparoscopic procedure has proven beneficial over traditional open surgery due to reduced trauma, improved healing and other attendant advantages.

A steerable laparoscopic or endoscopic instrument may provide a surgeon with a range of operability suitable for a particular surgical procedure. For example, the instrument may be configured such that the end effector may be aligned with a longitudinal axis of the instrument to facilitate insertion through a cannula, and thereafter, the end effector may be caused to articulate or move off-axis as necessary to appropriately position the end effector to engage tissue. When the end effector of a steerable, articulating instrument comprises a pair of jaw members for grasping tissue, the jaw members may need to be oriented relative to the tissue once properly positioned. Orienting the jaws may involve rotating the jaws about the longitudinal axis. However, this type of rotation may frustrate the positioning of the end effector. A roll joint disposed at a distal end of the elongated shaft may alleviate some of the difficulties and facilitate adjustments to either the position or the orientation of the jaws as the end effector approaches the targeted tissue.

One type of laparoscopic instrument is intended to generate a significant closure force between jaw members to seal small diameter blood vessels, vascular bundles or any two layers of tissue with the application electrosurgical or RF energy. The two layers may be grasped and clamped together by the jaws, and an appropriate amount of electrosurgical energy may be applied through the jaws. In this way, the two layers of tissue may be fused together. Many electrosurgical forceps include a conductor extending through the elongated to provide the end effector with an electrosurgical current. In some instances, the conductor may become entangled or may limit the range of motion achievable by the end effector. To offer a surgeon control of such an instrument a roll joint may be provided to facilitate passage of the electrosurgical current therethrough.

SUMMARY

The present disclosure describes a surgical instrument including a handle having an elongated shaft extending distally therefrom. The elongated shaft defines a longitudinal axis. An end effector extends distally from the elongated shaft and defines an end effector axis. The end effector is in communication with a source of electrosurgical energy. A roll joint couples the end effector to the elongated shaft and includes a first tubular structure extending distally from the elongated shaft, and a second tubular structure rotatably coupled to the first tubular structure about the end effector axis. The second tubular member supports the end effector such that the end effector is rotatable with respect to the first tubular structure about the end effector axis. A cable wrap volume is disposed within at least one of the first and second tubular structures, and a conductor for coupling the end effector with the source of electrosurgical energy is coiled about the end effector axis within the cable wrap volume. Rotation of the end effector about the end effector axis in a first direction unwinds the conductor.

The roll joint further may include a structural stop protruding from one or both of the first and second tubular structures to engage the other tubular structure to limit rotation of the end effector. The first and second tubular structures may be coupled to one another by a bearing set.

The elongated shaft may include an articulating portion disposed proximally of the roll joint wherein the articulating portion is flexible to permit pivotal motion of the end effector with respect to the longitudinal axis. The second tubular structure may be coupled to a drive member that extends through the articulating portion of the elongated shaft and is configured to transmit torque to the second tubular structure.

The end effector may include a pair of opposable jaw members movable between an open configuration for receiving tissue and a closed configuration for maintaining a closure pressure on the tissue. The end effector may be coupled to a reciprocating member that is longitudinally movable to induce movement of the jaw members between the open and closed configurations. The reciprocating member may extend through a longitudinal bore through the roll joint.

According to another aspect of the disclosure a surgical instrument includes a handle having an elongated shaft extending distally from the handle. The elongated shaft includes a proximal portion coupled to the handle and a distal portion pivotally coupled to the proximal portion. The proximal portion defines a longitudinal axis. An end effector defines an end effector axis and is in communication with a source of electrosurgical energy by an electrosurgical conductor extending through the elongated shaft. A roll joint is disposed between the distal portion of the elongated shaft and the end effector. The roll joint includes a first tubular structure coupled to the distal portion of the elongated shaft and a second tubular structure coupled to the end effector. The second tubular structure is rotatably coupled to the first tubular structure such that the end effector is rotatable about the end effector axis.

The electrosurgical conductor may be coiled about the end effector axis within the first tubular structure such that rotation of the end effector about the end effector axis unwinds the electrosurgical conductor. Alternatively, the electrosurgical conductor may be coupled to a conductive slip ring disposed within the first tubular structure, and an electrically conductive receptor may be coupled to the second tubular structure such that the receptor maintains electrical contact with the slip ring regardless of the rotational position of the second tubular structure with respect to the first tubular structure.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 7 is an enlarged, cross-sectional, partial perspective view of the drive mechanism in a third configuration for effecting a shoulder roll of the distal end of the instrument;

DETAILED DESCRIPTION

Figure 1:
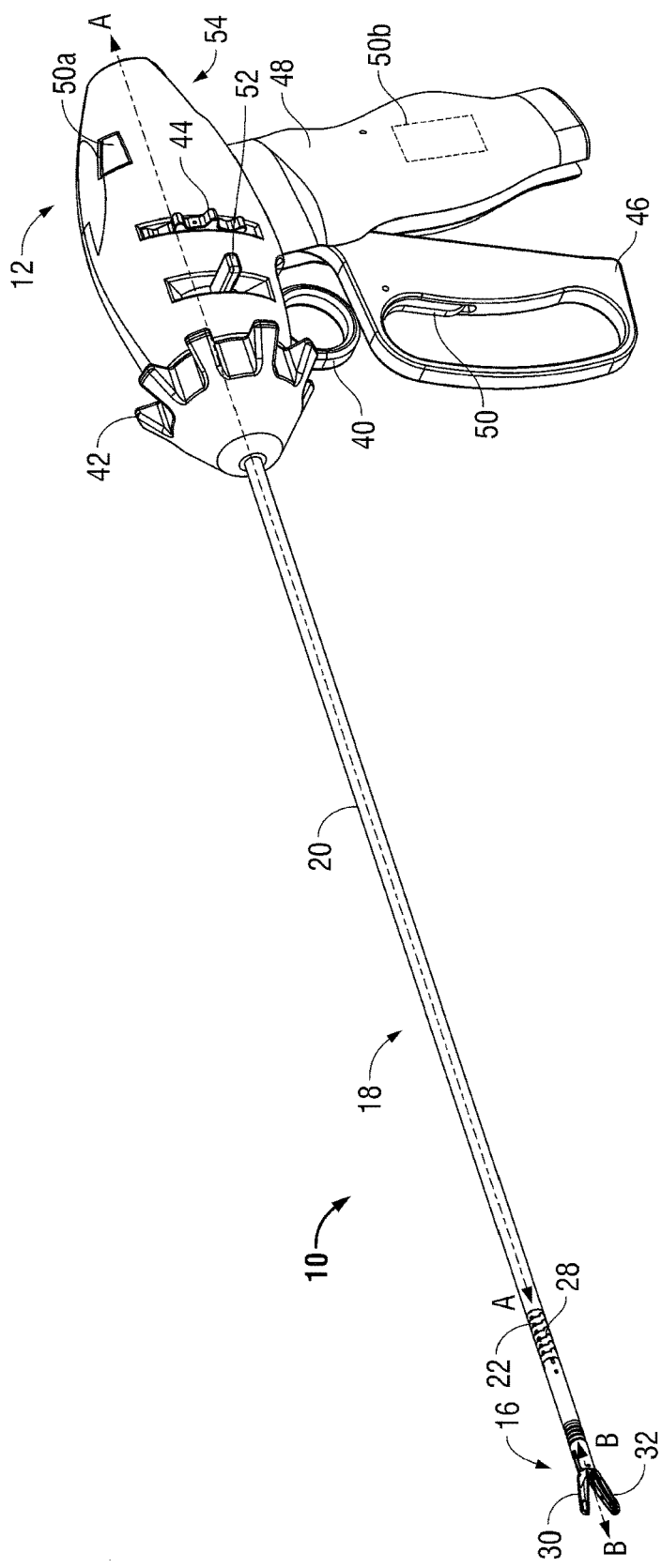
FIG. 1 is a perspective view of a surgical instrument in accordance with the present disclosure including an end effector aligned with a longitudinal axis.

Referring initially to FIG. 1, a steerable endoscopic instrument is depicted generally as instrument 10. Instrument 10 includes a handle 12 near a proximal end, an end effector 16 near a distal end and an elongated shaft 18 therebetween. Elongated shaft 18 includes a proximal portion 20 extending from the handle 12 and an articulating distal portion 22 supporting the end effector 16. The proximal portion 20 defines a longitudinal axis A-A, and is sufficiently long to position the end effector 16 through a cannula (not shown). At least one joint 28 is established between the proximal and distal portions 20, 22 of the elongated shaft 18 permitting the distal portion 22 and the end effector 16 to articulate or pivot relative to the longitudinal axis A-A as described in greater detail below (see FIG. 2A). The end effector 16 defines an end effector axis B-B, which is aligned with the longitudinal axis A-A when the articulating distal portion 22 of the elongated shaft 18 is in a "home" configuration.

The end effector 16 includes a pair of opposing jaw members 30 and 32. The jaw members 30, 32 are operable from the handle portion 12 to move between an open configuration to receive tissue, and a closed configuration (see FIG. 2D) to clamp the tissue and impart an appropriate clamping force thereto. When the end effector 16 is in the open configuration, a distal portion of each of the jaw members 30, 32 is spaced from the distal portion of the other of the jaw members 30, 32. When the end effector 16 is in the closed configuration, the distal portions of the jaw members 30, 32 are closer together. The end effector 16 is configured for bilateral movement wherein both jaw members 30 and 32 move relative to the end effector axis B-B as the end effector 16 is moved between the open and closed configurations. However, unilateral motion is also contemplated wherein one of the jaw members, e.g., 32 remains stationary relative to the end effector axis B-B and the other of the jaw members, e.g., 30 is moveable relative to the axis B-B.

Handle 12 is manipulatable by the surgeon from outside a body cavity to control the positioning, orientation and operation of the end effector 16 when the end effector 16 is positioned inside the body at a tissue site. To provide this operability, the handle 12 supports various actuators that are operable to induce movement in the end effector 16 through various modes. These actuators include an articulation trigger 40, which is operable to articulate the distal portion 22 of the elongated shaft 18 with respect to the longitudinal axis A-A (see FIG. 2A), a shoulder roll knob 42, which is operable to rotate the articulating distal portion 22 about the longitudinal axis A-A (see FIG. 2B), and a wrist roll knob 44, which is operable to rotate the end effector 16 about the end effector axis B-B (see FIG. 2C). The articulation trigger 40, wrist roll knob 44 and shoulder roll knob 42 cooperate to permit the end effector 16 to be appropriately positioned and oriented in a three dimensional environment to effectively engage tissue. Once the end effector 16 is positioned and oriented, the surgeon may approximate a pivoting handle 46 relative to a stationary handle 48 to move the jaw members 30, 32 to the closed position (see FIG. 2D).

The surgeon may also manipulate a finger trigger 50 to lock the pivoting handle 46 in an approximated position with respect to the stationary handle 48, and thus maintain the jaw members 30, 32 in the closed configuration. When the jaw members 30, 32 are in the closed configuration, the surgeon may initiate the delivery of electrosurgical energy to the jaw members 30, 32 by manipulating a push button 50a provided on the handle 12. In alternate embodiments, the delivery of electrosurgical energy may be initiated with the finger trigger 50.

Additionally, handle 12 supports a locking lever 52 that is operable to prevent unintended actuation of the articulation trigger 40 and shoulder roll knob 42. Thus, the end effector 16 may be maintained in a stable position. Also, a knife spool 54 is supported at a proximal end of the handle 12. The knife spool 54 is operable to advance a knife blade 54a (see FIG. 2B) through the jaw members 30, 32. With the exception of the finger trigger 50 and the push button 50a, each of the actuators described above transmits mechanical motion to the end effector 16 through a drive assembly 100 (see FIG. 3). The operation of the drive assembly 100 is discussed in greater detail below.

Push button 50a is in electrical communication with a source of electrosurgical energy such as electrosurgical generator 50b. The electrosurgical generator 50b serves to produce electrosurgical energy and also to control and monitor the delivery of the electrosurgical energy. Various types of electrosurgical generators 50b, such as those generators provided by Covidien—Energy-based Devices, of Boulder, Colo., may be suitable for this purpose. Electrosurgical generator 50b may be housed within the stationary handle 48 as depicted schematically in FIG. 1, or may alternatively be electrically and mechanically coupled to the instrument 10 by a cable (not shown). The electrosurgical generator 50b is in electrical communication with at least one of the jaw members 30, 32.

Figure 2A:
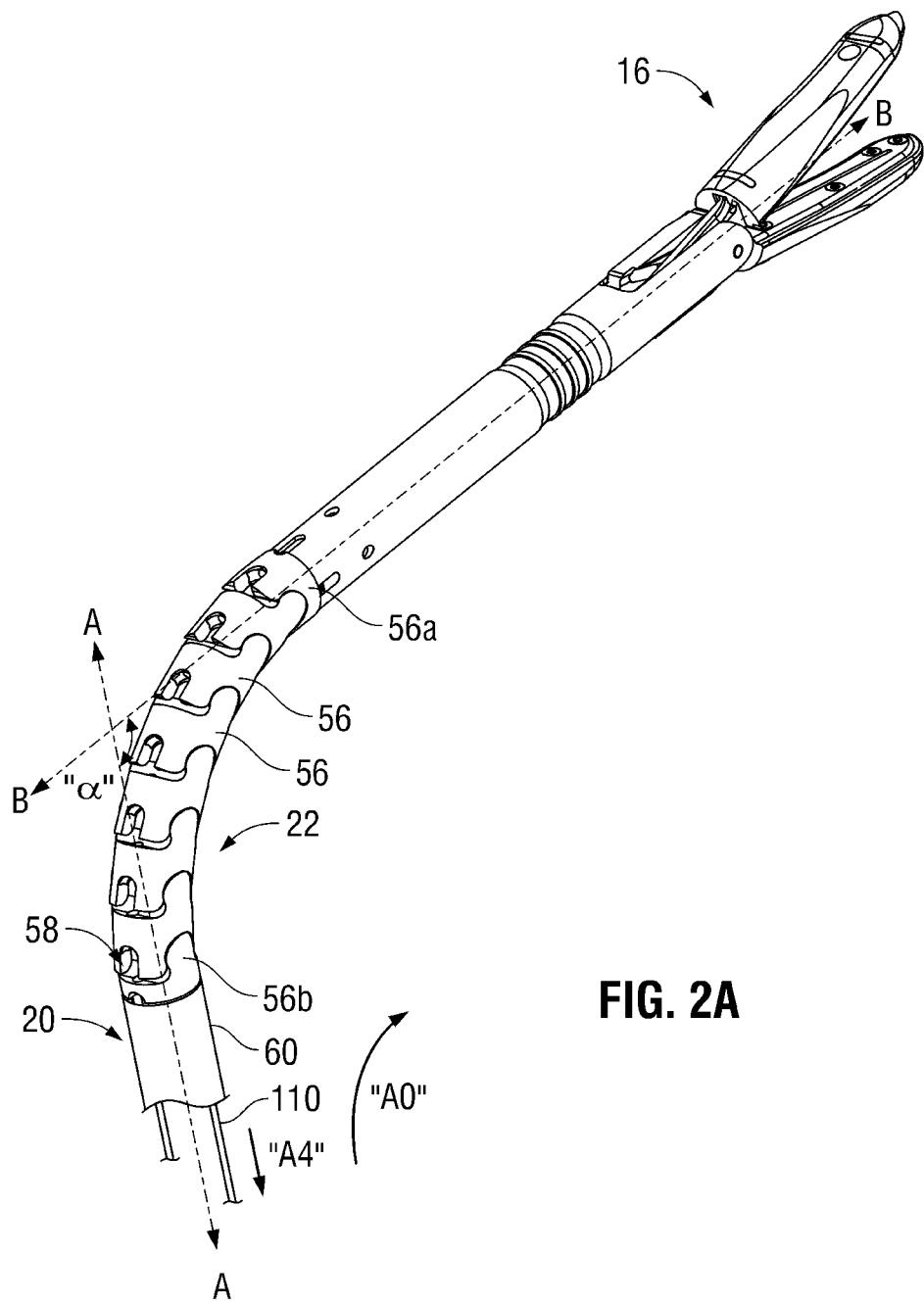
FIG. 2A is a partial, perspective view of a distal end of the instrument of FIG. 1 depicting the end effector in an articulated position with respect to the longitudinal axis.

Referring now to FIG. 2A, the end effector 16 is moved in an articulation mode in the direction of arrow "A0," or generally to the right from a perspective of a user. In this articulated position, the end effector axis B-B is oriented at an articulation angle "α" with respect to the longitudinal axis A-A. Any angle "α" may be achieved by bending distal portion 22 of the elongated shaft 18 to an appropriate degree. The distal portion 22 includes a plurality of segments 56 that are nested with one another such that each segment 56 is pivotally arranged with respect to a neighboring segment 56. Each segment 56 is constructed in a similar manner and includes a pair of steering bores 58 extending therethrough. The steering bores 58 are laterally arranged near an outer circumference of the link 56 and have a radial spacing of about 180 degrees. Thus, the steering bores 58 define a plane of articulation in which the distal 22 may bend. Although the distal portion 22 of the elongated shaft 18 may articulate in a single plane of articulation, other embodiments are also envisioned in which additional steering bores (not shown) permit articulation in multiple planes of articulation.

Figure 4:
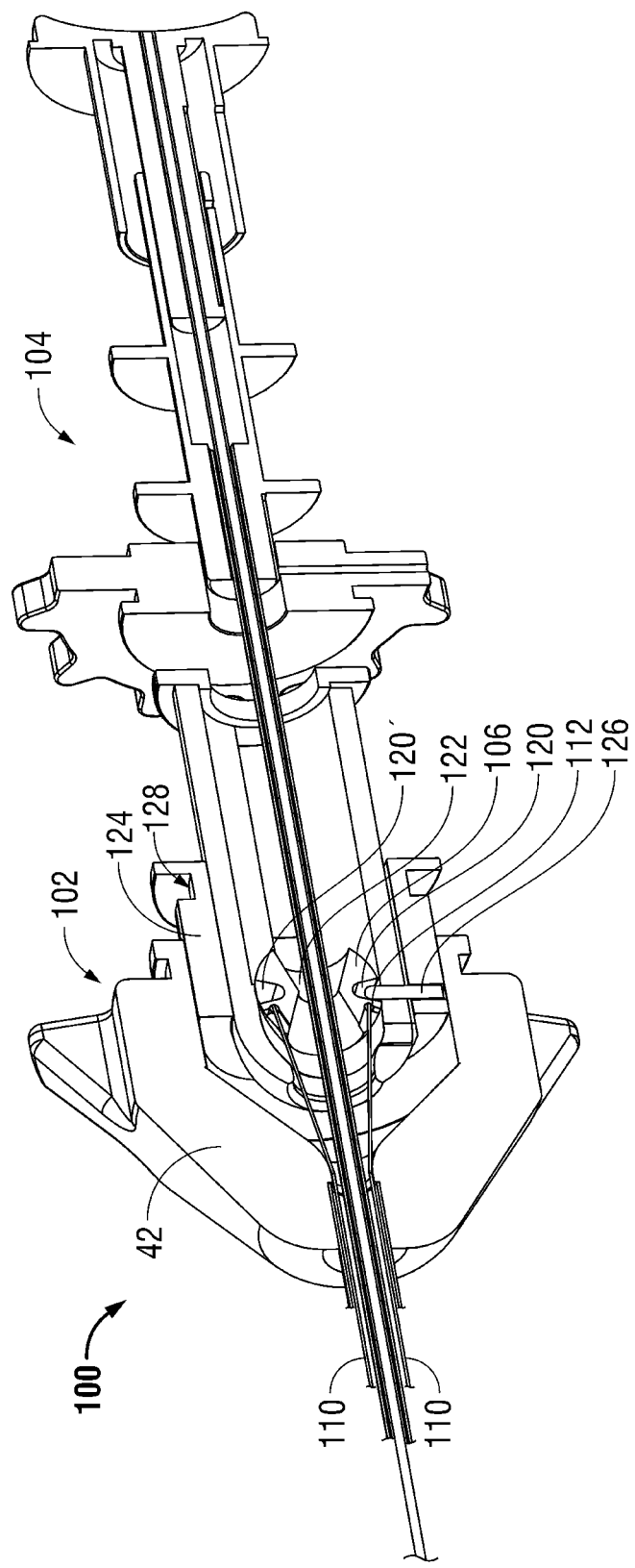
FIG. 4 is a cross-sectional perspective view of the drive mechanism of FIG. 3 in a first or "home" configuration for maintaining the end effector in alignment with the longitudinal axis.

The steering bores 58 permit passage of a pair of steering tendons 110 (see also FIG. 4). The steering tendons 110 are coupled to a leading segment 56a such that a tension imparted to one of the steering tendons 110 is transferred to the leading segment 56a. Thus, the distal portion 22 of the elongated shaft 18 may be articulated. For example, a tendon 110 disposed through the bores 58 on the right side of the distal portion 22 may be pulled proximally in the direction of arrow "A4" to draw the right side of the leading segment 56a proximally, and to curve the distal portion 22 to the right. Similarly, the distal portion 22 may be curved to the left by drawing the opposite tendon 110 proximally.

Each of the segments 56 includes a central bore (not shown) extending therethrough. The central bore permits passage of various components through the distal portion 22 to the end effector 16. For example, an electrosurgical conductor 178 (FIG. 10A) may pass through the distal portion 22 to provide electrosurgical energy to the end effector 16. Control cables, flexible rods, and torsion members may also be passed through the central bores to transfer mechanical motion to the end effector 16 as discussed in greater detail below. Although the distal portion 22 of the elongated shaft 18 has been described as including a plurality of pivoting segments 56, other embodiments are contemplated in which a single pivot joint is provided to orient the end effector axis B-B at angle "α" with respect to the longitudinal axis A-A.

Figure 2B:
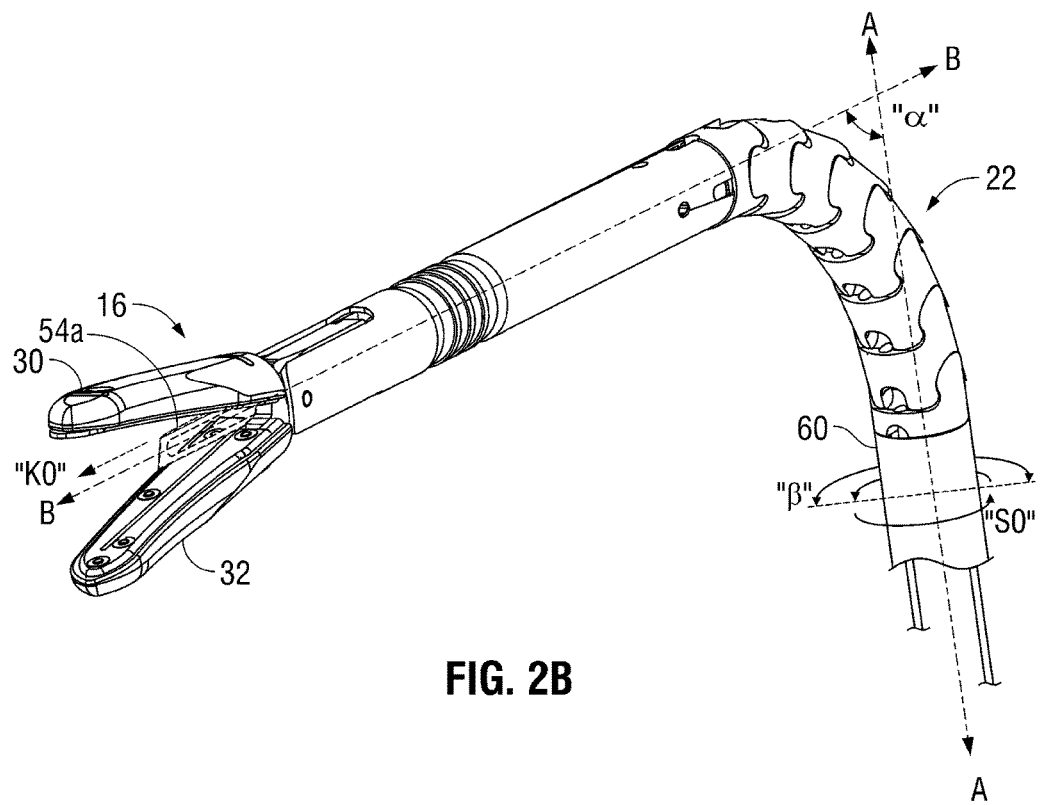
FIG. 2B is a partial, perspective view of the distal end of the instrument of FIG. 2A depicting the end effector in a rotated position with respect to a shoulder axis.

Referring now to FIG. 2B, the end effector 16 is moved through a second mode of motion herein referred to as a "shoulder roll." In the shoulder roll mode, the end effector 16, the distal portion 22 of the elongated shaft 18 and an outer tubular member 60 of the elongated shaft are all concurrently rotated about the longitudinal axis A-A as indicated by arrows "S0." The end effector 16 is maintained at the angle "α," and is swept through a three dimensional arc "β" such that the position of the end effector 16 is moved from the right generally to the left from the perspective of a user. The shoulder roll may be continued until any desired angle "β" is achieved. Since any angle "α" and any angle "β" is achievable, the end effector 16 may be positioned at any appropriate position in a three dimensional environment.

A knife blade 54a (depicted in phantom) is advanceable through the jaw members 30, 32 in the direction of arrow "K0" in a cutting mode as described in greater detail below with reference to FIG. 12. The embodiment of instrument 10 described herein includes a knife lock mechanism (see FIG. 13) to prevent the knife blade 54a from advancing to the position depicted in FIG. 2B when the end effector 16 is in the open configuration. Other embodiments are envisioned, however, which permit the knife blade 54a to be advanced when the end effector 16 is in the open configuration.

Figure 2C:
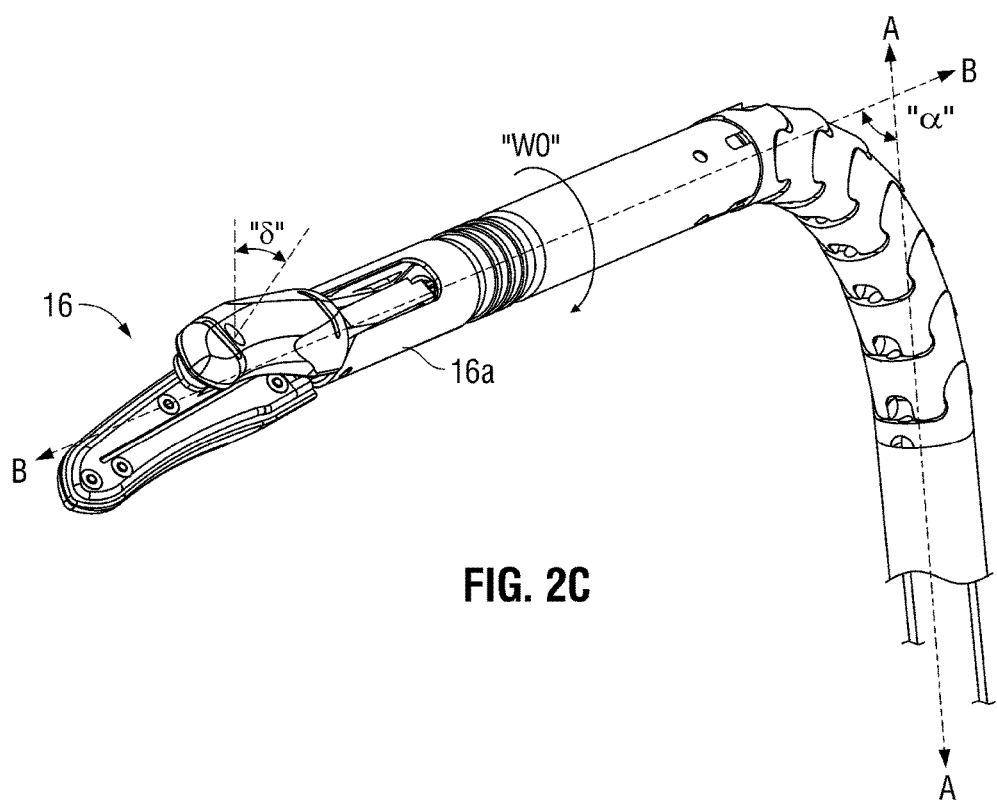
FIG. 2C is a partial, perspective view of the distal end of the instrument of FIG. 2B depicting the end effector in a rotated position with respect to a wrist axis.
Figure 2D:
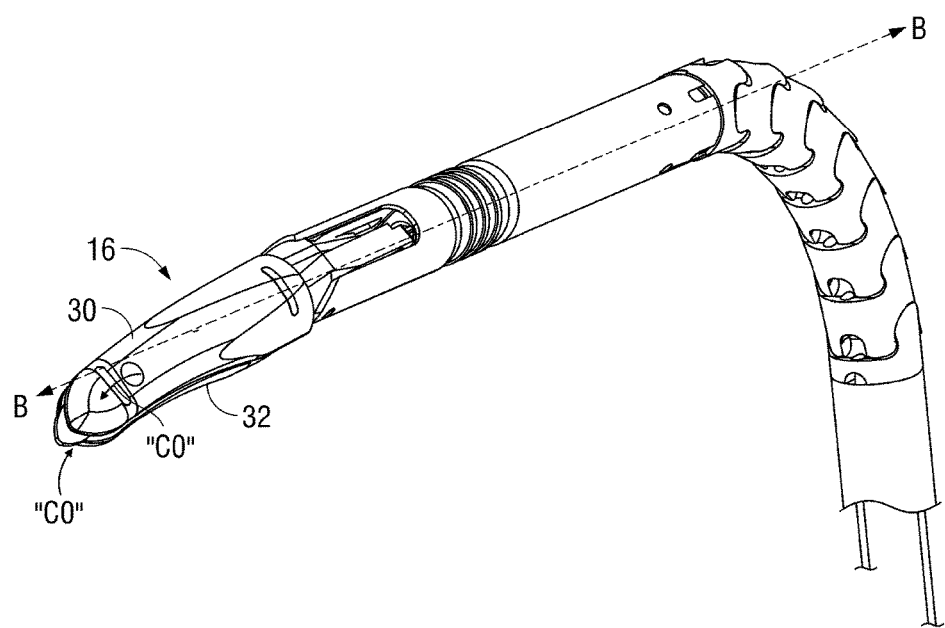
FIG. 2D is a partial perspective view of the distal end of the instrument of FIG. 2C depicting the end effector in a closed configuration.

Referring now to FIG. 2C, the end effector 16 is moved through a third mode of motion herein referred to as a "wrist roll." The wrist roll may be initiated by rotating the wrist roll knob 44 (FIG. 1) in either direction. The end effector 16 is rotated about the end effector axis B-B through any wrist roll angle "δ" until an orientation of the end effector 16 is achieved that is appropriate for contacting tissue. Once positioned and oriented, the end effector 16 may be moved through a fourth mode of motion herein referred to as the "clamping mode." The clamping mode may be initiated to move the jaw members 30, 32 in the direction of arrows "C0" to the closed configuration depicted in FIG. 2D to capture tissue therebetween. In this closed configuration, an appropriate clamping force along with electrosurgical energy may be delivered to the tissue to seal the tissue. Thereafter, the surgeon may elect to sever the tissue captured between the jaws 30, 32 by advancing the knife blade 54a (FIG. 2B) through the tissue in a fifth mode of motion herein referred to as the "cutting mode."

Figure 3:
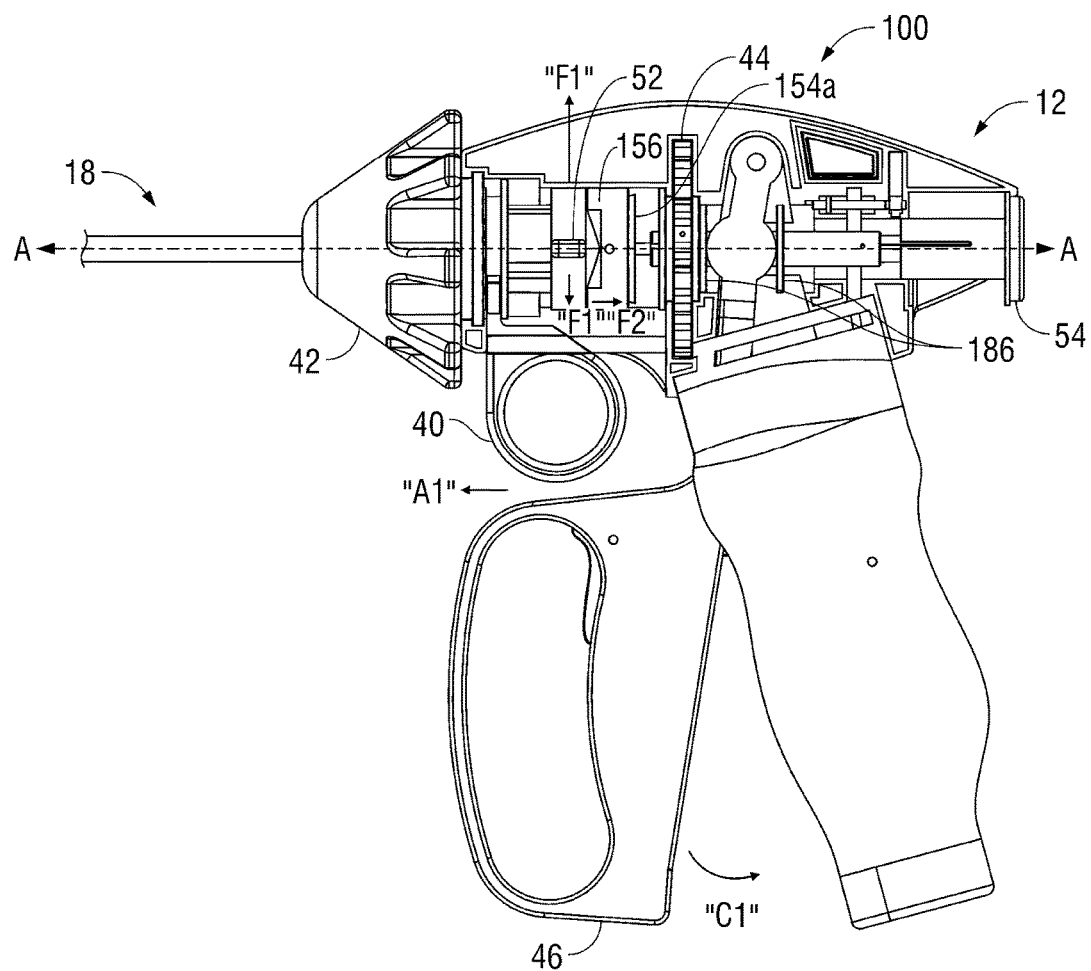
FIG. 3 is a partial side view of the instrument of FIG. 1 having a housing component removed and depicting a coaxial drive mechanism.

Referring now to FIG. 3, a coaxial drive assembly 100 is disposed generally within the handle 12. The coaxial drive assembly 100 receives mechanical motion from the actuators (e.g., articulation trigger 40, shoulder roll knob 42, wrist roll knob 44, pivoting handle 46, locking lever 52 and knife spool 54), and transmits a corresponding motion through the elongated shaft 18 to induce the various modes of motion in the end effector 16 discussed above. The mechanical motion transmitted through the elongated shaft 18 is either longitudinal motion directed in a general direction parallel to the longitudinal axis A-A, or rotational motion about the longitudinal axis A-A. Accordingly, the drive assembly 100 may be referred to as "coaxial."

Referring now to FIG. 4, the coaxial drive assembly 100 is depicted in a first "home" configuration corresponding to the "home" configuration of the elongated shaft 18 depicted in FIG. 1. The drive assembly 100 includes two main subsystems 102 and 104. A first positioning subsystem 102 drives the articulation and shoulder roll modes, and provides a lock to maintain the end effector 16 at particular angles "α" and "β." The second subsystem 104 drives the wrist roll, clamping and cutting modes. The two subsystems 102, 104 operate independently of one another in that the operation one subsystem, e.g. 102, does not transfer motion to the other subsystem, e.g. 104.

Figure 14A:
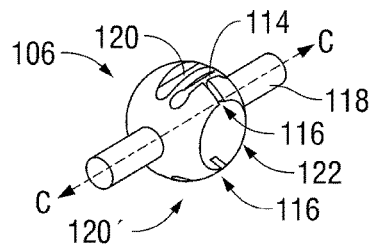
FIGS. 14A through 14D are perspective views depicting various individual components of the drive mechanism including an articulation sphere (14A), an articulation spool (14B), a shoulder roll knob (14C), and a locking collar (14D).

The first positioning subsystem 102 includes an articulation sphere 106 coupled to tendons 110 by a pair of tendon pins 112. The articulation sphere 106 (depicted in greater detail in FIG. 14A) is generally spherical in shape and includes a pair of coupling channels 114 (FIG. 14A) therein for receiving the tendon pins 112. The tendon pins 112 are captured within the connection channels 114, and the tendons 110 are secured to the tendon pins 112. Thus, the tendons 110 are coupled to the articulation sphere 106. Tendon relief slots 116 (FIG. 14A) extend longitudinally from the connection channels 114 and provide strain relief and permit rotational movement of the articulation sphere 106 without interfering with the tendons 110.

A pair of pivot axles 118 (FIG. 14A) extend laterally from the articulation sphere 106 in a diametrically opposed fashion. The pivot axles 118 define a pivot axis C-C (FIG. 14A) about which the articulation sphere 106 may be induced to pivot. A drive slot 120 is defined in the articulation sphere 106 laterally spaced from the pivot axis C-C such that longitudinal motion imparted to the drive slots 120 induces pivotal motion in the articulation sphere 106 about the pivot axis C-C. A second drive slot 120' is formed opposite drive slot 120. The second drive slot 120' provides additional symmetry to the articulation sphere 106 to ease manufacturing and assembly. However, second drive slot 120' is inactive in the embodiment of drive assembly 100 discussed herein with reference to FIG. 4, i.e., the second drive slot 120' is not engaged to impart pivotal motion to the articulation sphere 106. A central opening 122 is formed longitudinally through the articulation sphere 106. The central opening 122 permits passage of various components through the articulation sphere 106 without interference with the motion of the articulation sphere 106.

Figure 14B:
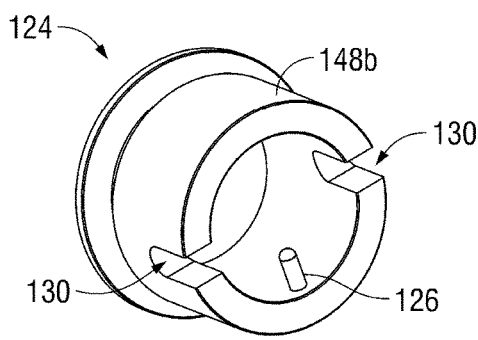

An articulation spool 124 (depicted in greater detail in FIG. 14B) is generally cylindrical in shape and radially surrounds the articulation sphere 106. A drive post 126 extends into an interior of the articulation spool 124 such that the drive post 126 may engage the drive slot 120 of the articulation sphere 106. A spool feature 128 at the proximal end of the articulation spool 124 provides a double-flange interface for engaging the articulation trigger 40 (see FIG. 3). Clearance slots 130 (FIG. 14B) are formed in the walls of the articulation spool 124 to provide clearance for the axles 118 of the articulation sphere 106.

Figure 5:
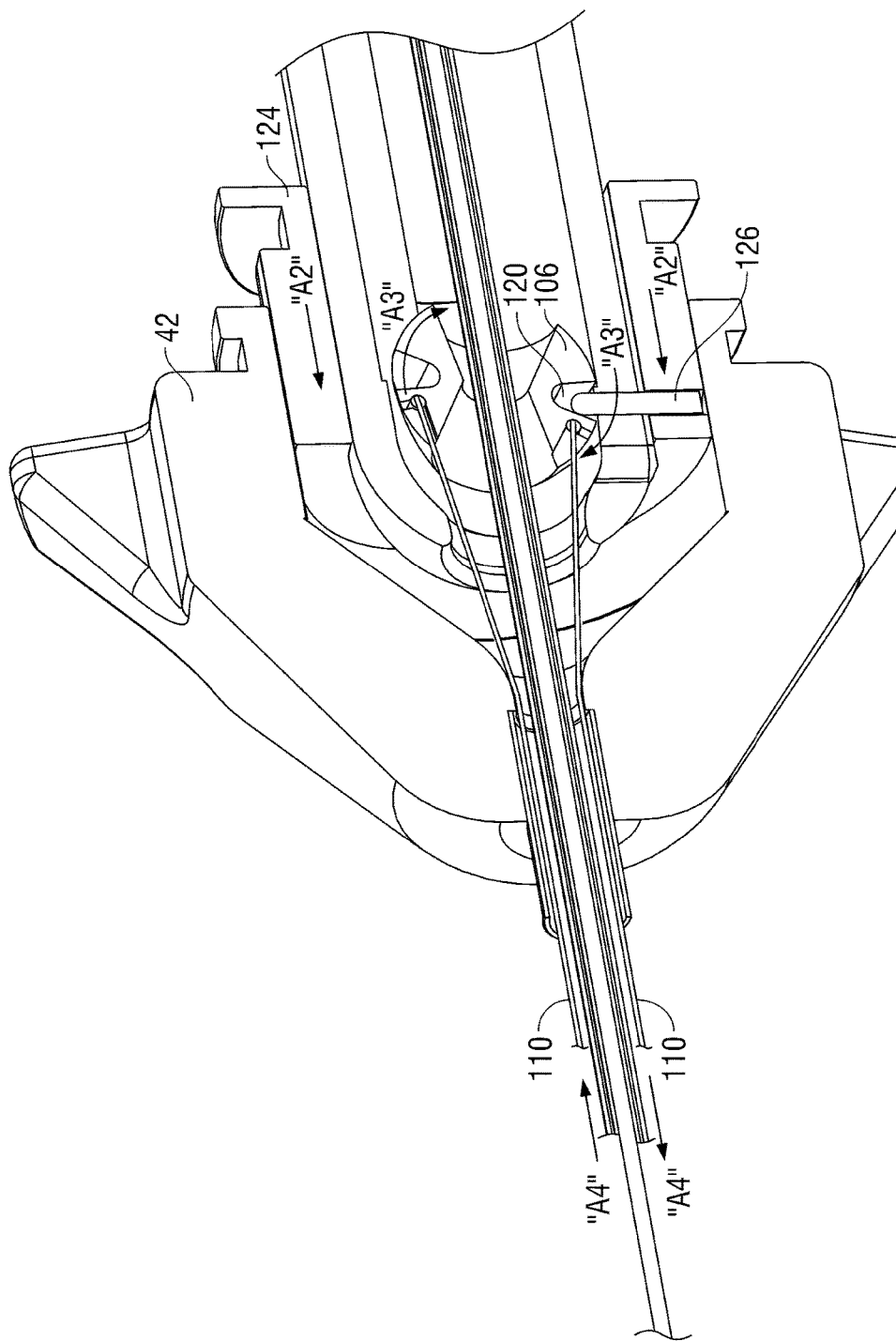
FIG. 5 is an enlarged, cross-sectional, partial perspective view of the drive mechanism in a second configuration for articulating the end effector with respect to the longitudinal axis.

Referring now to FIG. 5, the coaxial drive assembly is moved to a second configuration to initiate motion of the end effector 16 in the articulation mode. The articulation spool 124 may be driven longitudinally to induce rotational movement in the articulation sphere 106. For example, a surgeon may drive articulation trigger 40 distally in the direction of arrow "A1" (FIG. 3), which in turn drives the articulation spool 124 distally in the direction of arrows "A2." The drive post 126 drives the drive slot 120 distally, and since the axles 118 (FIG. 14A) of the articulation sphere 106 are longitudinally restrained (as discussed below), the articulation sphere 106 is induced to rotate in the direction of arrow "A3" about the pivot axis C-C. This rotation induces differential longitudinal tension and motion in the tendons 110 as indicated by arrows "A4." As discussed above with reference to FIG. 2A, differential longitudinal motion in the tendons 110 imparts movement in the end effector 116 in a first direction in the articulation mode. A surgeon may similarly induce articulation of the end effector 116 in an opposite direction by drawing the articulation trigger 40 proximally.

To induce motion of the end effector 16 in the articulation mode, the drive assembly 100 employs tension in the tendons 110 and a system spring rate. The tendons 110 are preloaded with a tensile force to manage the amount of slack or play in the articulation mode. In some instances, an adjustment to the amount of tension in the tendons may facilitate use of the coaxial drive assembly 100. For instance, over time, fatigue or creep tension losses may occur in the tendons 110. This loss in tension may be associated with a decline in responsiveness of the device 10, which may frustrate the intent of a surgeon. The ability to increase the tension in the tendons 110 may improve the survivability of the drive assembly 100 and facilitate operation of the instrument 10. In other instances, the general tension in the tendons 110 may be increased to prohibit any inadvertent movement of the end effector 16 in the articulation mode. In this manner, an operator may lock the end effector 16 at a particular angle "α" (FIG. 2A) with respect to the longitudinal axis A-A.

Figure 6A:
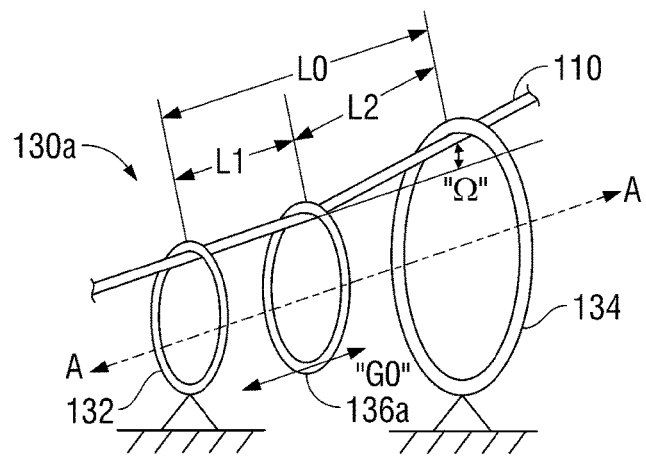
FIG. 6A is a schematic view of a tendon preload and locking device.

Referring now to FIG. 6A, a tendon preload-and-locking mechanism 130a may be incorporated into the device 10 at any convenient longitudinal location, and may be employed to adjust the tension in a tendon 110. The mechanism 130a includes first and second stationary tendon guides 132 and 134, respectively. Each of the stationary tendon guides 132, 134 is generally ring shaped and centered about the longitudinal axis A-A. The stationary tendon guides 132, 134 have a fixed longitudinal position with respect to the stationary handle 48 (FIG. 1), but in some embodiments may be free to rotate about the longitudinal axis A-A. Tendon 110 defines a tensile axis and is situated to extend through the rings and to contact an inner surface of each of the guides 132, 134. The first fixed tendon guide 132 has a smaller inner diameter than the second fixed tendon guide 134, and thus the tendon 110 extends obliquely with respect to the longitudinal axis A-A. The first fixed tendon guide 132 restrains the tendon 110 at a first lateral distance from the longitudinal axis A-A that is less than a second lateral distance from the longitudinal axis A-A at which the second fixed tendon guide 134 restrains the tendon 110. A straight-line distance between the points of contact between the tendon 110 and the stationary guides 132, 134 is represented by dimension "L0." Arranging the first tendon guide 132 distally with respect to the second fixed tendon guide 134 may direct the tendon 110 toward the longitudinal axis A-A for passage through the elongated shaft 18.

Arranged longitudinally between the stationary tendon guides 132, 134 is a movable guide 136a. Similar to the stationary tendon guides 132, 134, the movable guide 136a is ring shaped and centered about the longitudinal axis A-A. The movable guide 136a has an intermediate diameter, i.e., greater than the first stationary tendon guide 132 and less than the second stationary tendon guide 134 to restrain the tendon 110 at a third lateral distance from the longitudinal axis. The movable guide 136a is movable in the direction of arrow "G0" along the longitudinal axis A-A by an actuator (not shown), which is accessible to an operator at least during maintenance of the instrument 10. The movable guide 136a may be arranged such that an inner surface of the movable guide 136 contacts the tendon 110 as depicted in FIG. 6A, and exerts a force on the tendon 110 in the direction toward the longitudinal axis A-A. The tendon 110, thus assumes an angular configuration defining angle "Ω" with an apex at the movable guide 136a and forming straight-line segments between the movable guide 136a and each of the stationary guides 132, 134. These segments have lengths represented by the dimensions "L1" and "L2."

In this angular configuration, the total length (L1+L2) of the tendon 110 between the stationary guides 132, 134 is greater than the straight-line distance (L0) between the stationary guides 132, 134. Moving the movable guide 136a longitudinally in the direction of arrow "G0" toward the second stationary guide 134 increases the angle "Ω" and the total length (L1+L2) of the tendon 110 between the guides. This increase in length is associated with an increase in tension in the tendon 110 due to structural elastic deformation, compensating spring load, or elongation.

The longitudinal position of the movable guide 136a may be fixed at a location wherein an appropriate tension is maintained in the tendon 110 to suit a particular purpose. For example, the movable guide 136a may be moved sufficiently close to the second stationary guide 134 that the frictional force between the tendon 110 and the guides 132, 134, 136a is sufficient to effectively lock the position of the tendon 110. In this way, the tendon preload-and-locking mechanism 130a may be used to prevent inadvertent articulation of the end effector 16.

Figure 6B:
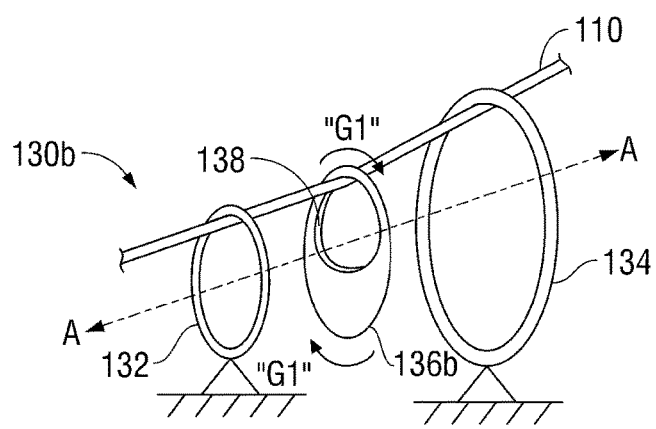
FIG. 6B is a schematic view of an alternate embodiment of a tendon preload and locking device depicting a movable guide having a cam surface.

Referring now to FIG. 6B, an alternate embodiment of a preload-and-locking mechanism is depicted generally as 130b. The mechanism 130b includes tendon 110 situated through stationary guides 132, 134 as described above with reference to FIG. 6A. A movable guide 136b includes an irregular inner profile defining a cam surface 138. The movable guide 136b may be rotated about the axis A-A in the direction of arrow "G1" to vary the distance from the axis A-A in which the tendon 110 contacts the cam surface 138. Thus, the path of tendon 110 between the stationary guides 132, 134 is varied along with the contact force encountered by the tendon 110 and the tension in tendon 110.

Figure 6C:
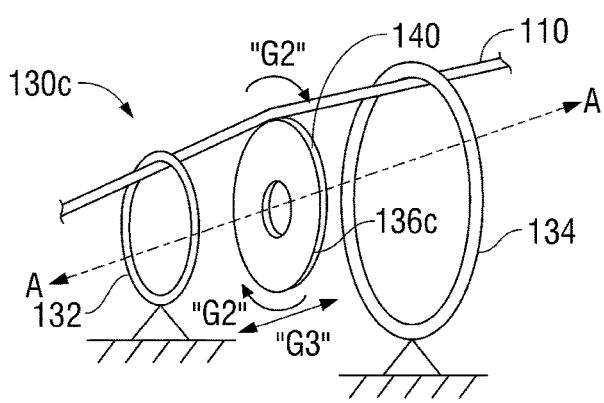
FIG. 6C is a schematic view of an alternate embodiment of a tendon preload and locking device depicting a movable guide for exerting an outwardly directed force on a tendon.

FIG. 6C depicts another embodiment of a preload-and-locking mechanism 130c in which a movable tendon guide 136c contacts tendon 110 in an opposite direction to bend the tendon 110 generally away from the longitudinal axis A-A. A cam surface 140 is provided on an outer surface of the movable tendon guide 136c to vary the distance from the longitudinal axis A-A in which the tendon contacts the tendon guide 136c. Thus, the tension in tendon 110 may be adjusted by rotating the movable tendon guide 136c about the longitudinal axis in the direction of arrow "G2." Alternatively, the tension may be adjusted by movement of the moveable tendon guide 136c in the longitudinal direction of arrow "G3" toward the first tendon 132 to increase the tension in the tendon.

Referring now to FIG. 7, the coaxial drive assembly 100 is moved to a third configuration inducing the end effector 16 to move in the shoulder roll mode. A surgeon may engage external bosses 142 on the shoulder roll knob 42 to rotate the shoulder roll knob 42 about the longitudinal axis A-A in the direction of arrows "S1." The shoulder roll knob 42 is fixedly coupled to the outer tubular member 60 of the elongated shaft 18, and thus the outer tubular member 60 rotates in the direction of arrow "S2" along with the shoulder roll knob 42. A distal end of the outer tubular member 60 is fixedly coupled to a trailing segment 56b (FIG. 2A) of the distal portion 22 of the elongated shaft 18. Thus, the entire distal portion 22 of the elongated shaft 18 rotates along with the shoulder roll knob 42 to achieve the motion in the shoulder roll mode.

Figure 14C:
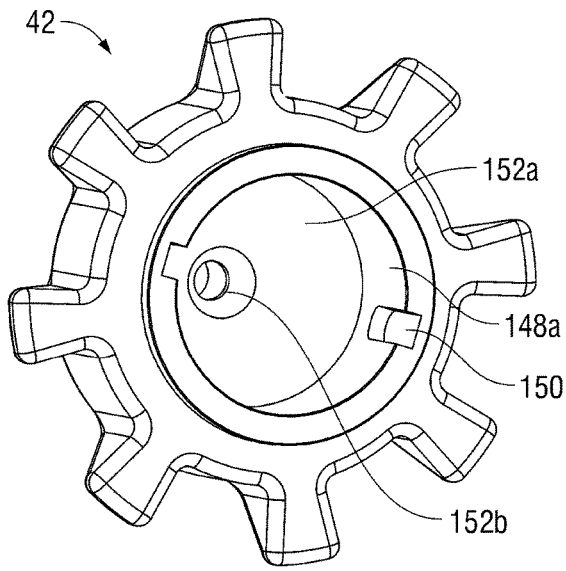

Rotation of the shoulder roll knob 42 induces a corresponding rotation in each element of the positioning subsystem 102 about the longitudinal axis A-A. An interior surface 148a (FIG. 14C) of the shoulder roll knob 42 may be splined to include ridges (not shown) extending longitudinally therein to correspond with longitudinal channels (not shown) on an exterior surface 148b (FIG. 14B) of the articulation spool 124. The ridges and channels allow the articulation spool 124 to move longitudinally within the interior of the shoulder roll knob 42 while providing a means for transmitting torque from the shoulder roll knob 42 to the articulation spool 124. This type of arrangement is hereinafter denoted a "splined slip joint."

Many of the other components of the coaxial drive assembly 100 may define a splined slip joint with radially adjacent components such that the radially adjacent components rotate together while maintaining independent longitudinal motion capabilities. For example, a splined slip joint is also defined between the articulation spool 124 and a locking collar 154. Thus, the locking collar 154 rotates along with the articulation spool 124 and the shoulder roll knob 42. The locking collar 154 is fixedly coupled to a flange 154a at a proximal end thereof. The flange 154a includes a series of radially oriented teeth and detents thereon, which may be engaged by a flexible rib (not shown) projecting from the stationary handle 48. Since the splined slip joints permit the flange 154a to rotate concurrently with the shoulder roll knob 42, the teeth on the surface of the flange 154a may be employed to index the shoulder roll mode and to provide a variable resistance lock for shoulder roll rotation. This indexed rotation of the flange 154a provides tactile feedback to the surgeon while employing the shoulder roll mode, and stabilizes the shoulder roll mode once an appropriate shoulder roll angle "β" (FIG. 2B) has been established. The splined slip joints also permit the locking collar 154 to move in a longitudinal direction to provide an additional lock to the articulation and shoulder roll modes as described below with reference to FIGS. 3 and 8.

The splined slip joints defined in the positioning subsystem 102 permit the entire positioning subsystem 102 to rotate concurrently to ensure that the tendons 110 do not become entangled in the shoulder roll mode. The articulation mode is thus independent of the shoulder roll mode in that the articulation mode may be initiated irrespective of the rotational position (e.g. the angle "β," FIG. 2B), of the end effector. Likewise, the shoulder roll mode may be initiated irrespective of the articulation angle (e.g. the angle "α," FIG. 2A).

The interior surface 148a (FIG. 14C) of the shoulder roll knob 42 includes clearance channels 150 therein. The clearance channels 150 are diametrically opposed to receive the axles 118 (FIG. 14A) of the articulation sphere 106. The axles 118 are longitudinally restrained in the clearance channels 150. The shoulder roll knob 42 also includes a tapered interior surface 152a extending between the interior surface 148 and a ring surface 152b. The tapered surface 152a may function as a conical volume feeder cone to guide the tendons 110 from the articulation sphere 106 to the ring surface 152b. The ring surface 152b guides the tendons 110 through the elongated shaft 18, and may serve as the first stationary tendon guide 132 as described above with reference to FIGS. 6A through 6C.

Figure 8:
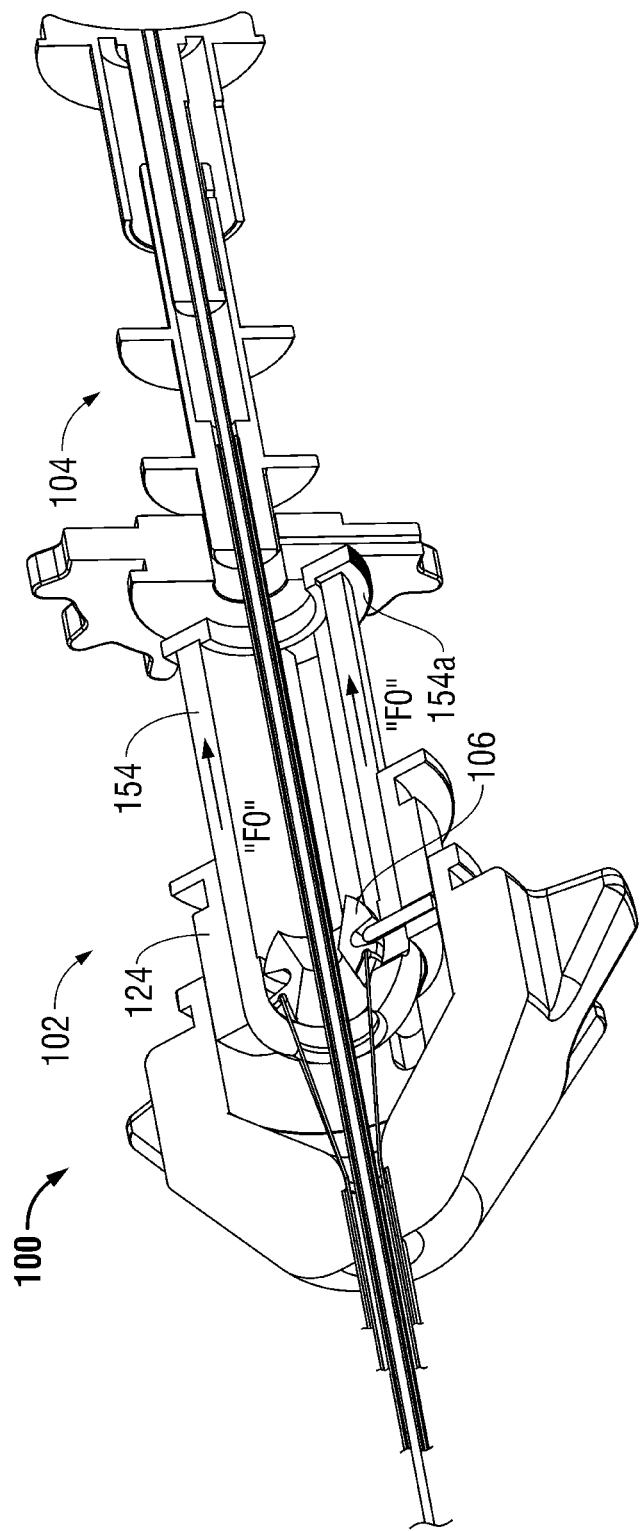
FIG. 8 is an enlarged, cross-sectional, partial perspective view of the drive mechanism in a fourth configuration for locking the distal end of the instrument in the shoulder roll configuration.

Referring now to FIGS. 3 and 8, the coaxial drive assembly 100 may be moved to a fourth configuration to prohibit motion of the end effector 16 in the articulation and shoulder roll modes simultaneously. When satisfactory articulation and shoulder roll positions have been achieved, a surgeon may manipulate locking lever 52 as depicted in FIG. 3 to induce appropriate movement of the locking collar 154 as depicted in FIG. 8. The locking lever 52 (FIG. 3) is supported to rotate about the longitudinal axis A-A in the direction of arrows "F1" and includes a cam surface on a proximal end thereof. The cam surface on the locking lever 52 engages a corresponding surface on a locking slider 156. The locking slider 156 is restrained from rotating by a splined slip joint with the handle portion 12 or a similar feature, and thus, rotation of the locking lever 52 in the direction of arrow "F1" induces longitudinal motion in the locking slider 156 in the direction of arrow "F2." The locking slider 156 engages the flange 154a that is coupled to locking collar 154 such that the longitudinal motion in the locking slider 156 is transmitted to the locking collar 154 as depicted in FIG. 8. The engagement of the locking slider 156 with the flange 154a permits the indexed rotational motion of the flange 154a in the shoulder roll mode as described above with reference to FIG. 7 while transmitting the longitudinal motion in the locking slider 156 to the locking collar 154.

Figure 14D:
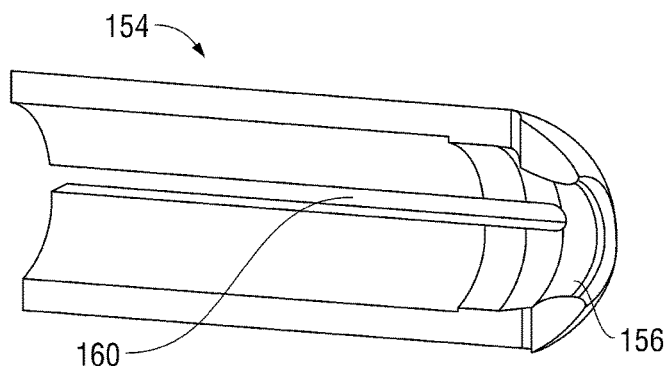

As depicted in FIG. 8, the locking collar 154 is induced to move in the direction of arrow "F0" in response to the longitudinal motion of the locking slider 156. The locking collar 154 is moved proximally in the direction of arrow "F0" until an interior concave surface 156 (FIG. 14D) of the locking collar 154 contacts the articulation sphere 106. The articulation sphere 106 encounters a frictional resistance to motion since the tendons 110 exhibit a fixed length, and thus do not permit the articulation sphere 106 to move proximally. The frictional resistance to motion prohibits the articulation sphere 106 from pivoting about the pivot axis C-C (FIG. 14A) and thus prohibits motion of the end effector 16 in the articulation mode.

The frictional resistance generated between the locking collar 154 and the articulation sphere 106 also supplements the resistance to rotation provided by the indexing feature on the flange 154a as discussed above with reference to FIG. 7. The frictional resistance between the articulation sphere 106 and the locking collar 154 discourages rotation of the locking collar 154 about the longitudinal axis A-A. As discussed above, the locking collar 154 may include longitudinal ridges and channels on an outer surface thereof to define a splined slip joint with corresponding ridges and channels on an interior of the articulation spool 124. The locking collar 154 includes longitudinal slots 160 (FIG. 14D) therein to permit passage of the axles 118 of the articulation sphere 106 and the drive post 126 of the articulation spool 124. The frictional resistance to rotation in the locking collar 154 may thus be transmitted to the articulation spool 124, and further to the shoulder roll knob 42 through the splined slip joint defined between articulation spool 124 and the shoulder roll knob 42. Thus, the locking collar 154 provides a more positive stop to the shoulder roll mode than the indexing feature on the flange 154a alone.

Figure 9:
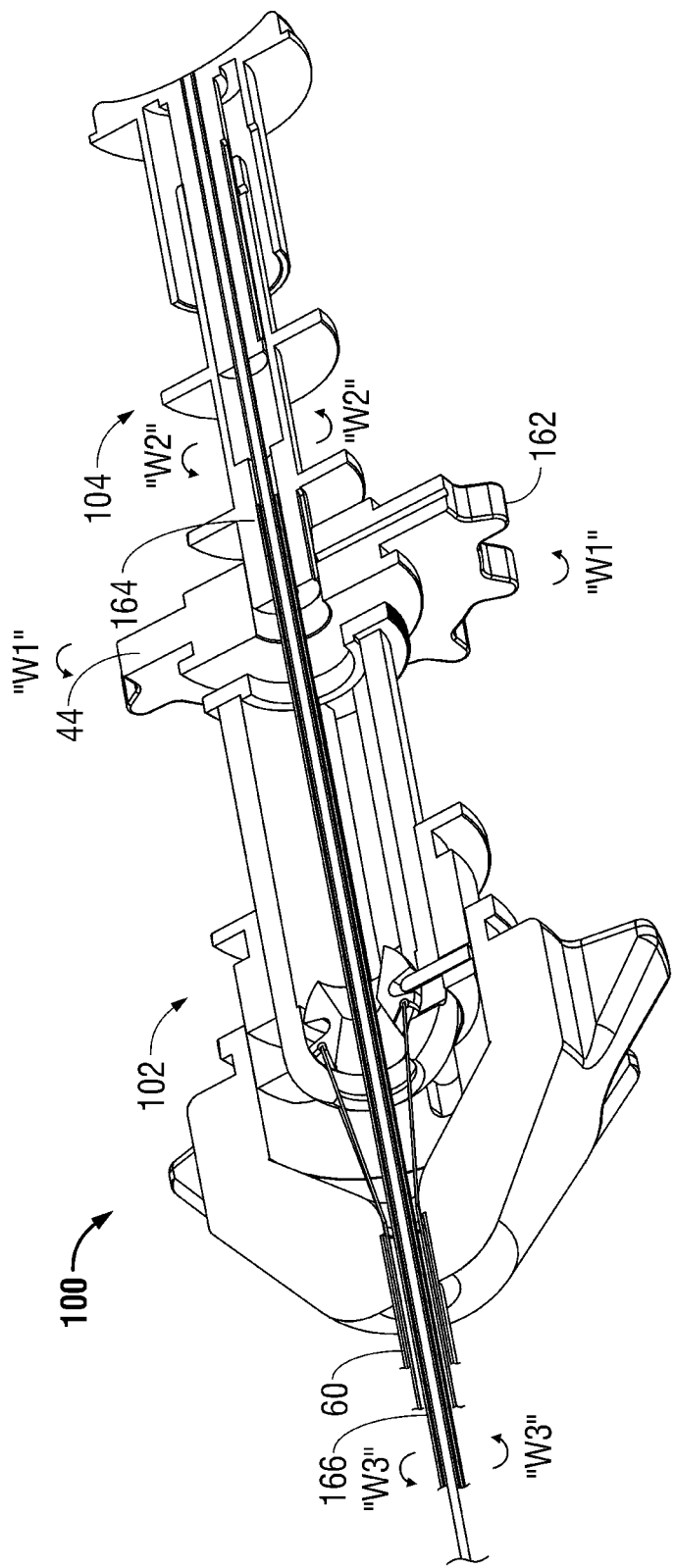
FIG. 9 is an enlarged, cross-sectional, partial perspective view of the drive mechanism in a fifth configuration for effecting a wrist roll of end effector.
Figure 10A:
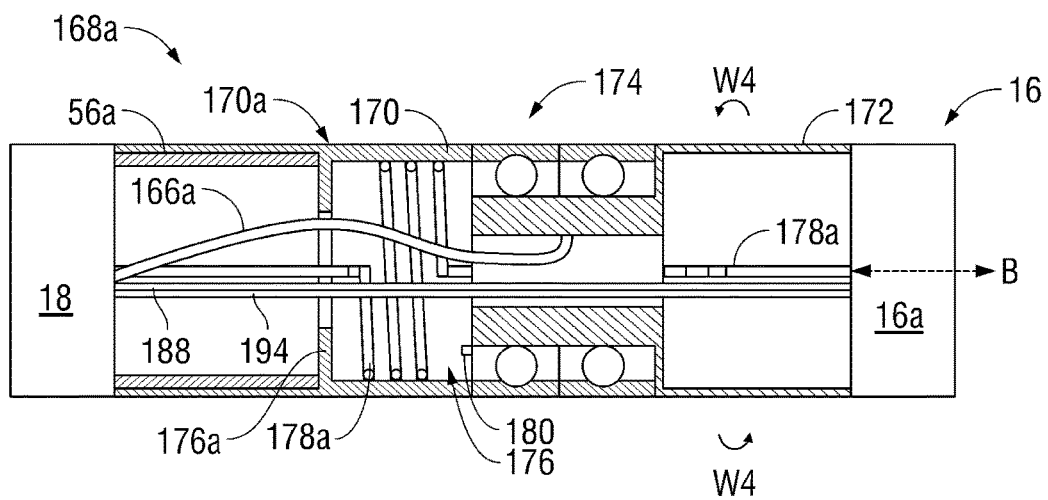
FIG. 10A is schematic view of a wrist roll joint at the distal end of the instrument.

Referring now to FIG. 9, the coaxial drive assembly 100 is moved to a fifth configuration to induce the end effector 16 to move in the wrist roll mode. The wrist roll mode is driven by subsystem 104, which operates independently of the positioning subsystem 102. Thus, the wrist roll mode, and the other modes of motion driven by the subsystem 104, may be initiated irrespective of the configuration of the positioning subsystem 102. To initiate the wrist roll mode, a surgeon may engage external bosses 162 on the wrist roll knob 44 to rotate the wrist roll knob 44 about the longitudinal axis A-A in the direction of arrows "W1." The wrist roll knob 44 is coupled to a jaw spool 164 through a splined slip joint such that the jaw spool 164 rotates in the direction of arrow "W2" along with the wrist roll knob 44. The jaw spool 164 is fixedly coupled to an intermediate tubular member 166 of the elongated shaft 18, and thus the intermediate tubular member 166 rotates in the direction of arrow "W3" along with the wrist roll knob 44. The intermediate tubular member 166 extends distally through the positioning subsystem 102 and through the outer tubular member 60. A distal end of the intermediate tubular member 166 is coupled to a torsion cable 166a (FIG. 10A), which transmits torque from the intermediate tubular member 166 to a roll joint 168a (FIG. 10A). The roll joint 168 supports the end effector 16, and thus the torque transmitted to the roll joint 168a may induce the end effector 16 to rotate in the wrist roll mode. The torsion cable 166a is flexible, and extends through the articulating distal portion 22 of the elongated shaft 18 such that torque may be transmitted through the distal portion 22 regardless of the articulation angle "α" achieved.

Referring now to FIG. 10A, the torsion cable 166a extends to a roll joint 168a. The roll joint 168a includes a first tubular structure 170 and a second tubular structure 172. The first tubular structure 170 extends distally from the elongated shaft 18 where a shoulder 170a is provided to rigidly couple the first tubular structure 170 to leading segment 56a. The second tubular structure 172 is rigidly coupled to an end effector housing 16a (see also FIG. 2C) that supports the end effector 16. The first and second tubular structures 170, 172 are coupled to one another by a bearing set 174, which permits the second tubular structure 172 to rotate relative to the first tubular structure 170 about end effector axis B-B. The bearing set 174 may be provided as a duplex pair, e.g. a pre-manufactured pair of bearings with a precisely controlled distance between races to provide a particular pre-load to the bearings, and may be fixedly coupled to the first and second tubular structures 170, 172 by welding or a similar process. The torsion cable 166a is coupled to the second tubular structure 172 to transmit torque thereto. When the intermediate tubular member 166 (FIG. 9) is induced to rotate in the direction of arrow "W3" (FIG. 9) by the rotation of the wrist roll knob 44, the torsion cable 166a induces the second tubular structure 172 to rotate in the direction of arrows "W4." Since the second tubular structure 172 is rigidly coupled to the end effector housing 16a, the end effector 16 may be moved through the wrist roll mode in the direction of arrows "W0" (FIG. 2C) about the end effector axis B-B.

The first tubular structure 170 includes a cable wrap volume 176 therein to provide sufficient space for electrosurgical conductor 178 to be coiled about the end effector axis B-B. The cable wrap volume 176 extends between a bulkhead 176a and the bearing set 174. The electrosurgical conductor 178 is configured to conduct electrosurgical energy to the end effector 16 in response to an appropriate actuation of finger trigger 50 and/or push button 50a (FIG. 1). Conductor 178 may exhibit a round, flat or other geometry to facilitate winding or unwinding of the conductor 178 within the cable wrap volume 176. Winding the conductor 178a permits the end effector 16 to rotate in the wrist roll mode without unduly straining or tangling the conductor 178a. Sufficient slack is provided in the conductor 178a to permit rotation of the end effector 16 in either direction. The number of wrist roll rotations permitted may be limited by the geometric construction and winding configuration of the conductor 178a. To relieve any undue strain on the conductor 178 that may occur as a result of reaching the limit of wrist-rolls, a structural stop 180 may be provided. The structural stop 180 is positioned such that the second tubular structure 172 engages the stop 180 to prohibit further rotational motion before the slack in the conductor 178a is taken up. First and second tubular structures 170, 172 are include a longitudinal bore extending therethrough to permit passage of various implements to effect motion in the end effector 16. For example, a reciprocating member 188 is longitudinally movable in the clamping mode to open and close the jaws, and compression member 194 is longitudinally movable in the cutting mode to advance the knife blade.

Figure 10B:
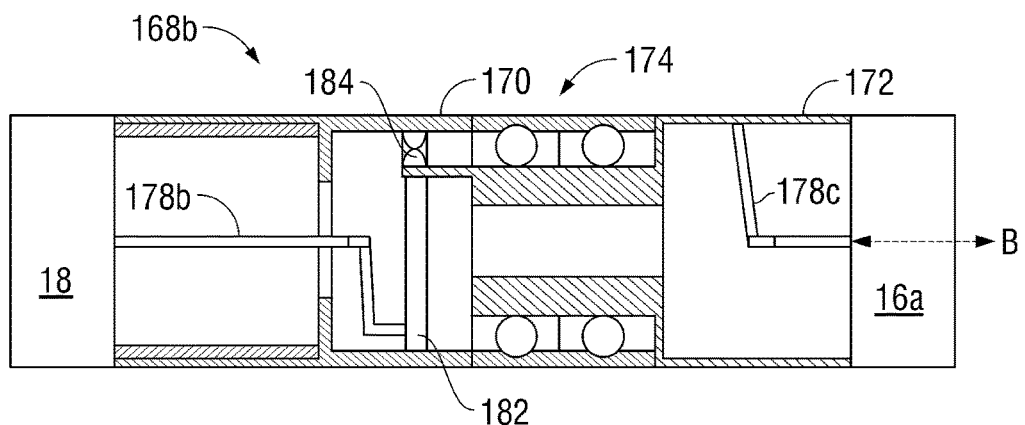
FIG. 10B is a schematic view of an alternate embodiment of a roll joint.

Referring now to FIG. 10B, an alternate embodiment of a roll joint is depicted generally as 168b. The roll joint 168b includes a bearing set 174 coupled between first and second tubular structures 170, 172 as described above with reference to FIG. 10A. An electrosurgical conductor 178b extends to an electrically conductive slip ring 182 defined on the interior of first tubular member 170. An electrically conductive receptor 184 is coupled to the second tubular structure 172 such that the receptor 184 maintains electrical contact with the slip ring 182 regardless of the wrist roll angle "γ" (FIG. 2C) achieved. The receptor 184 is in electrical communication with the end effector 16 through electrosurgical conductor 178c, and thus the end effector 16 may be provided with an electrosurgical current. The slip ring arrangement of roll joint 168b permits an unlimited number of wrist roll rotations of the end effector 16.

Figure 11:
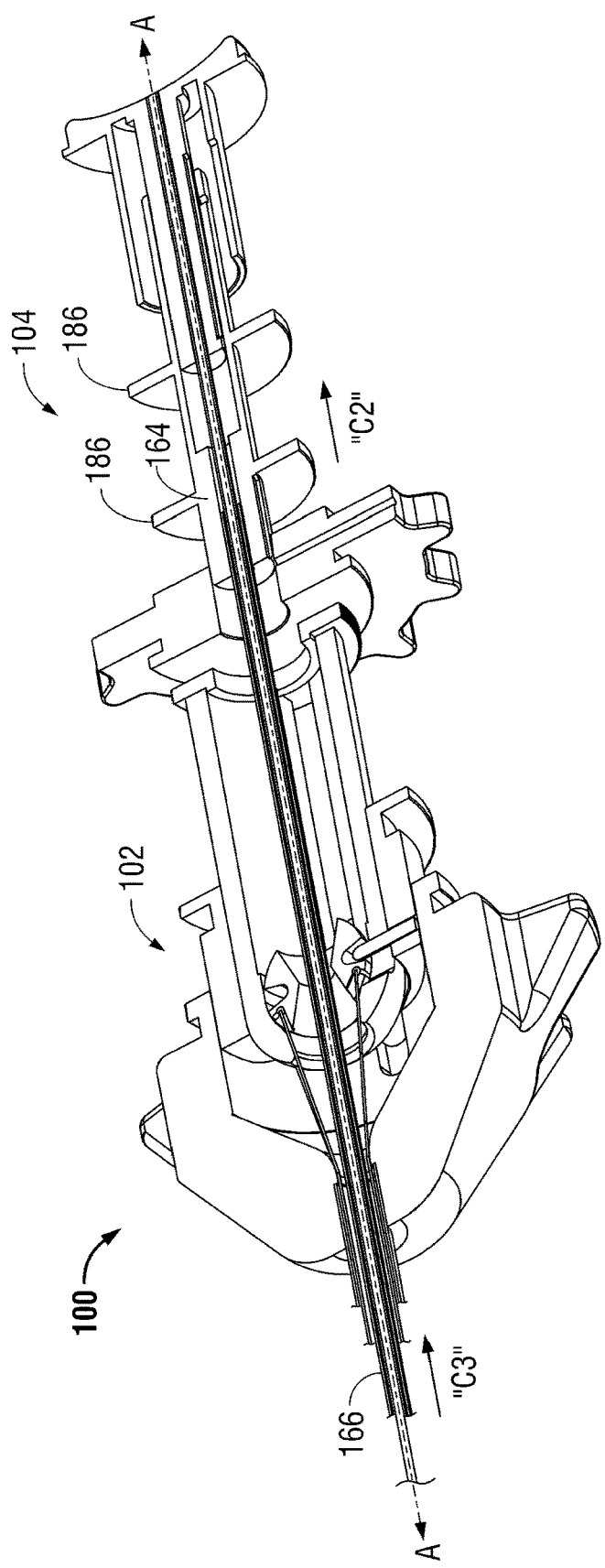
FIG. 11 is an enlarged, cross-sectional, partial perspective view of the drive mechanism in a sixth configuration for closing a pair of jaw members at the end effector.

Referring now to FIG. 11, the coaxial drive assembly 100 is moved to a sixth configuration for moving the end effector 16 in the clamping mode. As discussed above with reference to FIG. 1, the clamping mode may be initiated to open and close the jaw members 30, 32. To close the jaws 30, 32, (see FIG. 2D) the jaw spool 164 is moved longitudinally in the proximal direction of arrow "C2" by the approximation of the pivoting handle 46 with the stationary handle 48 in the direction of arrow "C1." The pivoting handle 46 engages the jaw spool 164 between drive flanges 186 such that jaw spool 164 may be moved longitudinally in either direction by the approximation and separation of the pivoting handle 46 with respect to the stationary handle 48. Since the jaw spool 164 is fixedly coupled to the intermediate tube member 166 as described above with reference to FIG. 9, the proximal longitudinal motion in the jaw spool 164 is transmitted to the intermediate tube member 166. Thus, the intermediate tube member 166 moves in the proximal direction as indicated by arrow "C3."

A distal end of the intermediate tubular member 166 is coupled to a narrow reciprocating member 188 (FIG. 10A). The reciprocating member 188 transmits the proximal motion of the intermediate tube member 166 through the articulating distal portion 22 of the elongated shaft 18. The reciprocating member 188 may be a relatively thin wire or bar oriented such that the reciprocating member 188 is sufficiently flexible to bend in a single plane to accommodate any articulation angle "α" while remaining sufficiently rigid to transmit sufficient tensile and compressive forces to open and close jaw members 30, 32. The jaw members 30, 32 may include any appropriate feature such that the jaw members 30, 32 are induced to close by the proximal longitudinal motion in the reciprocating member 188. For example, the jaw members 30, 32 may exhibit cam features (not shown) thereon to transform the longitudinal motion of the reciprocating member 188 into pivotal motion of the jaw members 30, 32 as in the instrument described in U.S. Pat. No. 7,083,618 to Couture et al., entitled "VESSEL SEALER AND DIVIDER."

When the jaw members 30, 32 are moved to the closed configuration to clamp tissue therebetween, an electrosurgical tissue seal may be created. To form an effective tissue seal, in one embodiment, a relatively high clamping force is typically generated to impart a closure pressure on the tissue in the range of from about 3 kg/cm$^2$ to about 16 kg/cm$^2$. An appropriate gap distance of about 0.001 inches to about 0.006 inches may be maintained between the opposing jaw members 30, 32, although other gap distances are contemplated. Since at least one of the jaw members 30, 32 is connected to a source of electrical energy 50b (see FIG. 1), a surgeon may manipulate finger trigger 50 and/or push button 50a to initiate transmission of electrosurgical energy through tissue to effectuate a seal.

Figure 12:
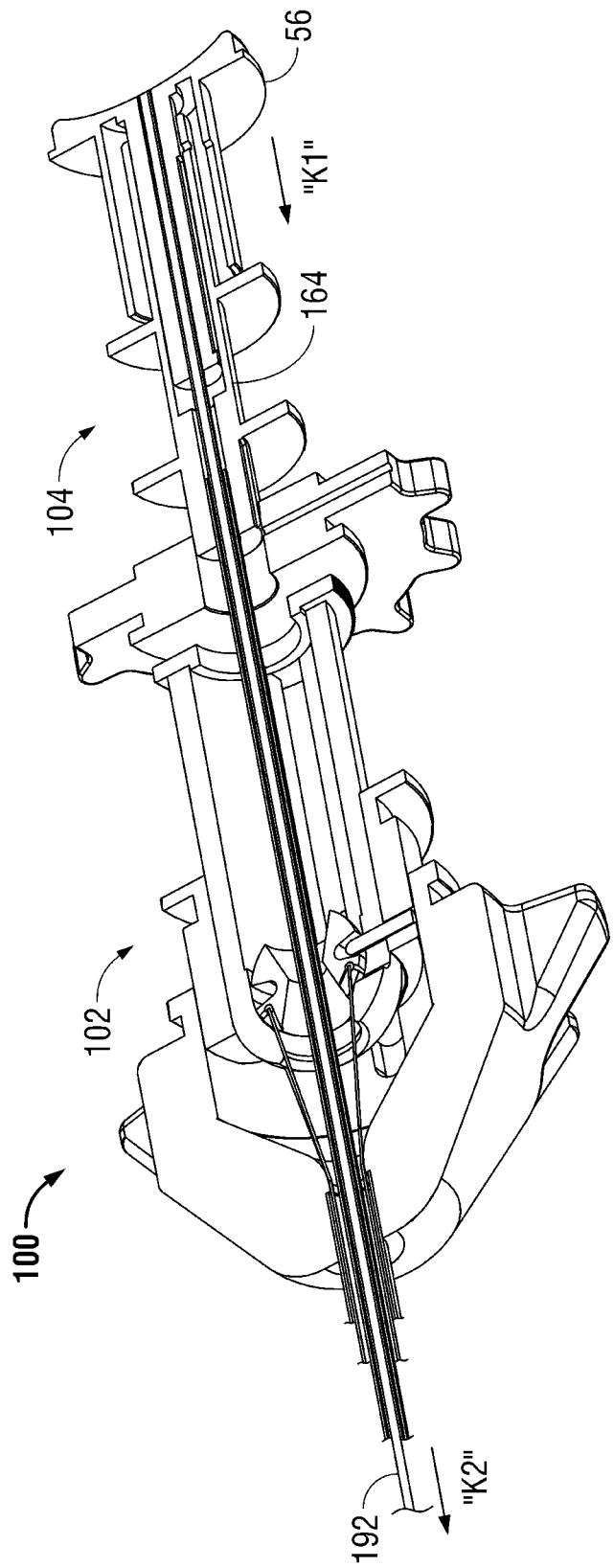
FIG. 12 is an enlarged, cross-sectional, partial perspective view of the drive mechanism in a seventh configuration for advancing a knife through the pair of jaw members.
Figure 13:
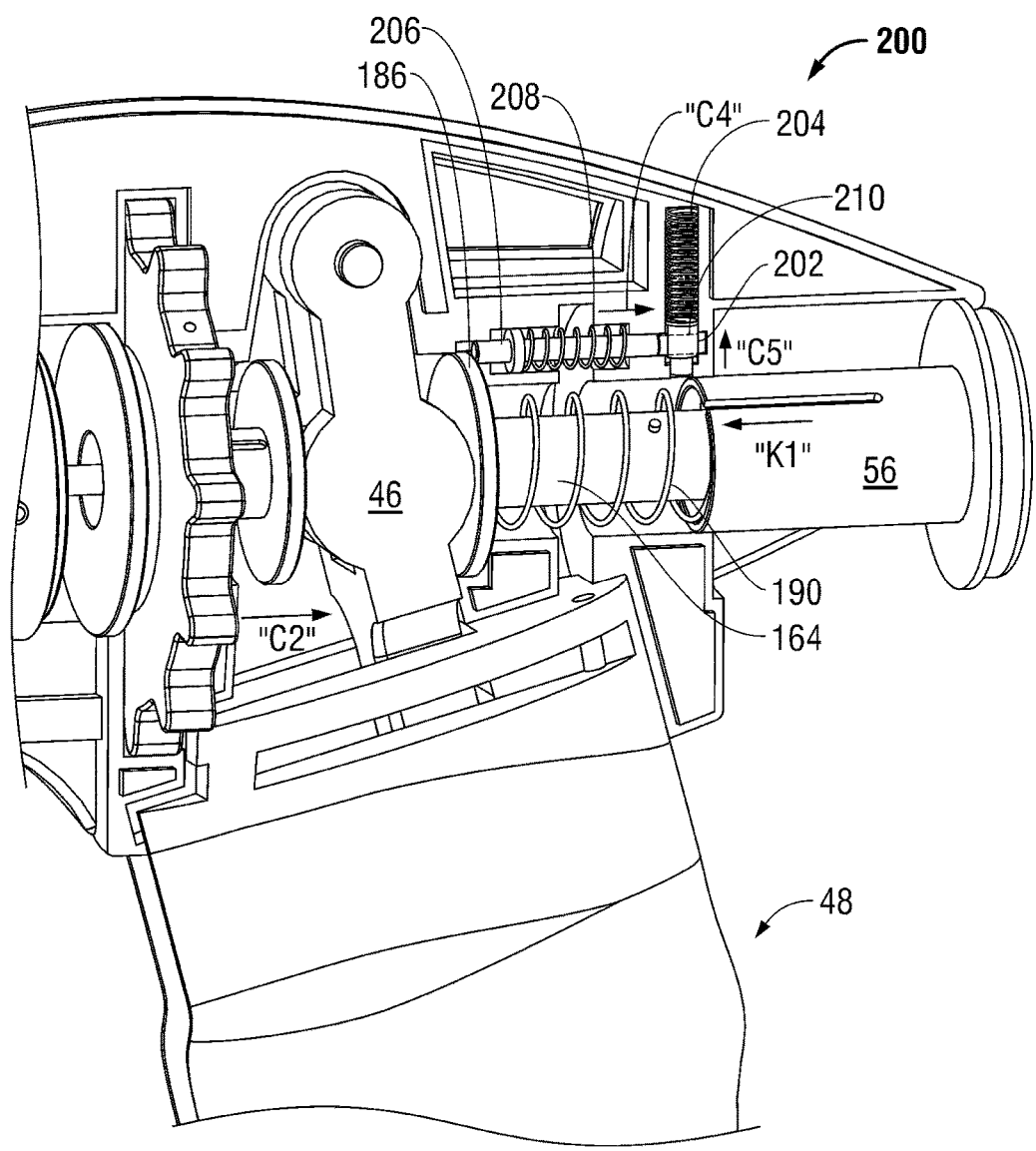
FIG. 13 is a partial side view of the instrument depicting a knife lock mechanism to permit advancement of the knife only after the pair of jaw members has been closed.

Referring now to FIG. 12, the coaxial drive assembly 100 is moved to a seventh configuration for advancing a knife blade 54a (see FIG. 2B) to induce end effector motion in the cutting mode. The knife blade may be advanced through the jaw members 30, 32 to sever or transect tissue once a tissue seal has been formed. The knife spool 56 forms a splined slip joint with the jaw spool 164 such that a surgeon may move the knife spool 56 longitudinally in the distal direction of arrow "K1" against the bias of a spring 190 (FIG. 13). The knife spool 56 is fixedly coupled to an inner tubular member 192 such that the distal longitudinal motion imparted to the knife spool 56 is transmitted to the inner tubular member 192. Thus, the inner tubular member 192 moves distally as indicated by arrow "K2." A distal end of the inner tubular member 192 is fixedly coupled to the bendable compression member 194 (FIG. 10A), which is configured similar to the reciprocating member 188 described above with reference to FIGS. 11 and 10A. Thus, the compression member 194 may transmit longitudinal motion through the articulating distal end 22 of the elongated shaft 18 regardless of the articulation angle "α" achieved. A distal end of the compression member 194 is, in turn, fixedly coupled to the knife blade 54a. Thus, the longitudinal motion imparted to the knife spool 56 may be transmitted ultimately to the knife blade 54a to drive the knife blade 54a through tissue. When the surgeon releases the knife spool 56, the bias of spring 190 tends to retract the knife blade 54a.

Referring now to FIG. 13, a knife lock mechanism is depicted generally as 200. The knife lock mechanism 200 is configured to permit advancement of the knife blade 54a (FIG. 2B) in the cutting mode only when the jaw members 30, 32 have been moved to the closed configuration depicted in FIG. 2D. The mechanism 200 includes a latch piston 202 mounted within the stationary handle 48. The latch piston 202 is normally biased by compression spring 204 to a position in which the latch piston 202 prohibits distal translation of the knife spool 56. A latch release piston 206 is biased by compression spring 208 in a distal direction such that a distal end of the latch release piston 206 abuts one of the flanges 186 of the jaw spool 164. A proximal end of the latch release piston 206 includes a ramped cam surface 210 in engagement with the latch piston 202.

A surgeon may approximate the pivoting handle 46 with the stationary handle 48 to induce longitudinal motion in the jaw spool 164 in the direction of arrow "C2" and thereby move the jaw members 30, 32 to the closed configuration as described above with reference to FIG. 11. The jaw spool 164 bears on the release piston 206 such that the release piston 206 moves in the proximal direction indicated by arrow "C4" against the bias of spring 208. As the release piston 206 moves proximally, the ramped cam surface 210 engages the latch piston 202 such that the latch piston 202 is induced to move in the direction of arrow "C5" against the bias of spring 204. The latch piston 202 is thereby moved to a position that does not interfere with longitudinal motion of the knife spool 56 in the direction of arrow "K1". Thus, motion in the cutting mode may be initiated. When the surgeon separates the pivoting handle 46 from the stationary handle 48, the bias of the springs 204 and 208 return the latch piston 202 to its normally biased position. In the normally biased position, the latch piston 202 extends into the path of the knife spool 56 prohibiting motion of the knife spool 56.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
    an elongated shaft having a proximal portion and a distal portion that are articulable relative to one another, the proximal portion defining a first axis and the distal portion defining a second axis; and
    a roll joint disposed at a distal end of the elongated shaft, the roll joint including:
        a first tubular structure extending distally from the elongated shaft and having an inner surface defining a cable wrap volume;
        a second tubular structure coupled to the first tubular structure, the second tubular structure rotatable about the second axis relative to the first tubular structure; and
        a conductor coiled against the inner surface about the second axis within the cable wrap volume such that rotation of the second tubular structure about the second axis in a first direction unwinds the conductor, the conductor extending from the proximal portion of the elongated shaft through the second tubular structure.

2. The instrument according to claim 1, further comprising an end effector disposed at a distal end of the second tubular structure, the conductor configured to connect the end effector to a source of electrosurgical energy through the proximal portion of the elongated shaft.

3. The instrument according to claim 2, wherein the proximal portion of the elongated shaft is rotatable about the first axis.

4. The instrument according to claim 3, further comprising a handle coupled to the proximal portion of the elongated shaft, proximal portion rotatable relative to the handle.

5. The instrument according to claim 4, wherein the handle includes the source of electrosurgical energy.

6. The instrument according to claim 2, wherein the end effector includes a pair of opposable jaw members movable between an open configuration for receiving tissue and a closed configuration for maintaining a closure pressure on the tissue.

7. The instrument according to claim 6, wherein the end effector is coupled to a reciprocating member longitudinally movable to induce movement of the jaw members between the open and closed configurations, the reciprocating member extending through a longitudinal bore defined through the roll joint.

8. The instrument according to claim 1, wherein the roll joint further comprises a structural stop protruding from at least one of the first and second tubular structures and engaging the other of the first and second tubular structures to limit rotation of the second tubular structure.

9. The instrument according to claim 1, wherein the first and second tubular structures are coupled to one another by a bearing set.

10. The instrument according to claim 1, wherein the second tubular structure is coupled to a drive member, the drive member extending through the roll joint and configured to transmit torque to the second tubular structure.

11. The instrument according to claim 10, wherein the elongated shaft includes an articulating portion between the proximal and distal portions, the drive member extending through the articulating portion.

12. The instrument according to claim 1, wherein a portion of the second tubular structure is disposed within the first tubular structure.

13. The instrument according to claim 1, wherein an outer surface of the first tubular structure forms a contiguous surface with an outer surface of the second tubular structure.

14. A surgical instrument, comprising:
    an elongated shaft having a proximal portion and a distal portion, the proximal portion defining a first axis and the distal portion defining a second axis, the proximal portion rotatable about the first axis; and
    a roll joint disposed at a distal end of the elongated shaft, the roll joint including:
        a first tubular structure extending distally from the elongated shaft and having an inner surface defining a cable wrap volume;
        a second tubular structure coupled to the first tubular structure, the second tubular structure rotatable about the second axis relative to the first tubular structure; and
        a conductor coiled against the inner surface about the second axis within the cable wrap volume such that rotation of the second tubular structure about the second axis in a first direction unwinds the conductor, the conductor extending from the proximal portion of the elongated shaft through the second tubular structure.

15. The instrument according to claim 14, wherein the elongated shaft includes an articulating portion between the proximal and distal portions configured to pivot the distal portion relative to the proximal portion.

16. The instrument according to claim 14, further comprising a handle coupled to the proximal portion of the elongated shaft, proximal portion rotatable relative to the handle.

* * * * *